United States Patent [19]

Lim et al.

[11] Patent Number: 5,118,323

[45] Date of Patent: Jun. 2, 1992

[54] BENZOXAZINE DYES

[75] Inventors: Mu-Ill Lim, Trumbull; Nancy A. Botta, Darien, both of Conn.

[73] Assignee: Clairol, Inc.

[21] Appl. No.: 751,459

[22] Filed: Aug. 29, 1991

Related U.S. Application Data

[62] Division of Ser. No. 440,567, Nov. 22, 1989, Pat. No. 5,055,110.

[51] Int. Cl.⁵ .................. A61K 7/13; C07D 263/52
[52] U.S. Cl. ............................ 8/405; 8/409; 8/429; 548/217
[58] Field of Search ............. 548/217; 8/405, 409, 8/429

[56] References Cited

U.S. PATENT DOCUMENTS 4,743,595  5/1988  Itoh et al. ........................... 544/111
5,055,387 10/1991  Diehl et al. ........................ 548/217

Primary Examiner—Mary C. Lee
Assistant Examiner—Joseph K. McKane
Attorney, Agent, or Firm—Doreen F. Shulman

[57] ABSTRACT

Novel benzoxazine compounds of the structure

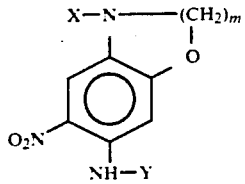

wherein X and Y are independently selected from the group hydrogen, alkyl, alkoxyalkyl, aminoalkyl, hydroxyalkyl and hydroxyaminoalkyl, each alkyl moiety having 1 to 6 carbons, and m=1, 2, or 3, have been found suitable as hair dyes.

7 Claims, No Drawings

BENZOXAZINE DYES

This is a division of application Ser. No. 440,567, U.S. Pat. No. 5,055,110 filed Nov. 22, 1989, entitled BENZOXAZINE DYES.

BACKGROUND

The use of nitro-substituted para-phenylenediamines as dyes for keratinaceous substrates is well known. See J. F. Corbett, *The Chemistry of Synthetic Dyes*, Vol. V., K. Venkataraman, ed., Academic Press., New York, p. 475 (1971). U.S. Pat. Nos. 3,591,638; 4,470,826 and 4,668,236, as well as Canadian Patents 806,152 and 935,094 describe the preparation and use of these types of dyes.

Hair dye chemists have long searched for substitutes for some of the simpler 2-nitro-p-phenylenediamine (2-NO$_2$-PPD) derivatives, e.g. 2-nitro-p-phenylenediamine, because of poor stability in cosmetic formulations and poor washfastness. However, many of the compounds suggested as substitutes for 2-NO$_2$-PPD do not possess the unique bright orange-red color and, therefore, represent poor substitutes. Indeed it has been shown that substitution on the amino group in the 2-nitro-p-phenylenediamine series gives absorption maxima at considerably longer wavelength. The color of these nitro dyes is shifted towards red-violet or violet rather than orange-red (See J. F. Corbett, *J. Soc. Cosmet. Chem.*, 35, 297, (1984)).

The basic structure of the target compounds is 3,4-dihydro-2H-1,4-benzoxazine. A number of approaches to the synthesis of this system have been reported since 1889.

Work on the synthesis of 1,4-benzoxazine was reported by Knorr at Berichte der Deutchen Chemischen Gesellschaft (Ber.) 22, 2085 (1889) and *Ber.* 55, 3818 (1922). Heating 2-(2-chloroethylamino)phenol 6a with alkali gave 1,4-benzoxazine 7a.

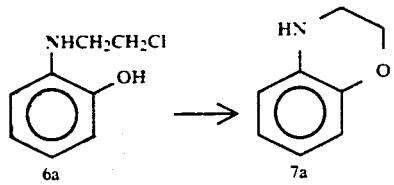

Compound 7a was also synthesized from 2-(2-hydroxyethylamino)-anisole 8a under acidic condition using hydrochloric acid at 160°-180° C. (A. Fairbourne and H. Toms, *J. Chem. Soc.*, 119, 2076 (1921)).

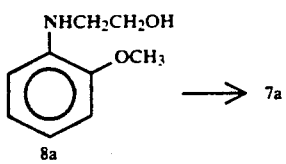

Hill and Ramage reported at *J. Chem. Soc.*, 3709 (1964) a convenient synthesis of 7-methoxy-1,4-benzoxazine from 2-amino-5-methoxyphenol 9a. Compound 9a reacted with chloroacetyl chloride in acetone to give 2-chloroacetamido-5-methoxy phenol 10a. An intramolecular cyclization of 10a with aqueous sodium hydroxide produced 7-methoxy-3-oxo-1,4-benzoxazine 11a, which upon reduction with lithium aluminum hydride in THF resulted in the formation of 7-methoxy-3,4-dihydro-2H-1,4-benzoxazine 12a.

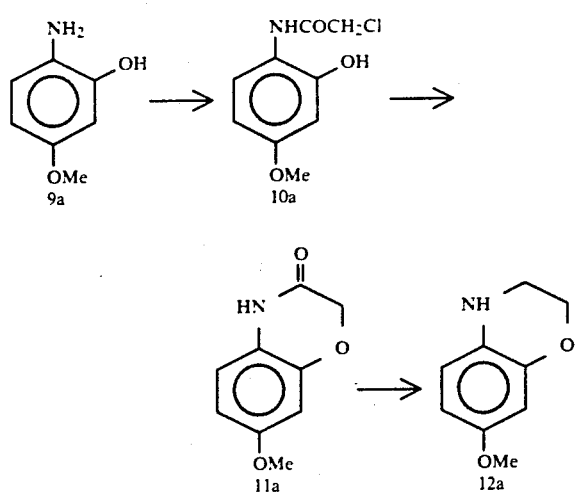

In U.S. Pat. Nos. 3,690,810 and 3,817,995, L'Oreal reported the synthesis of 6-hydroxy (or amino)-3,4-dihydro-2H-1,4-benzoxazine 15a (or 19a) as an oxidation coupler. Reaction of 2-amino-4-methoxyanisole 13a with 2-bromoethanol and calcium carbonate in water gave compound 14a. Subsequent cyclization of 14a with HBr afforded 15a.

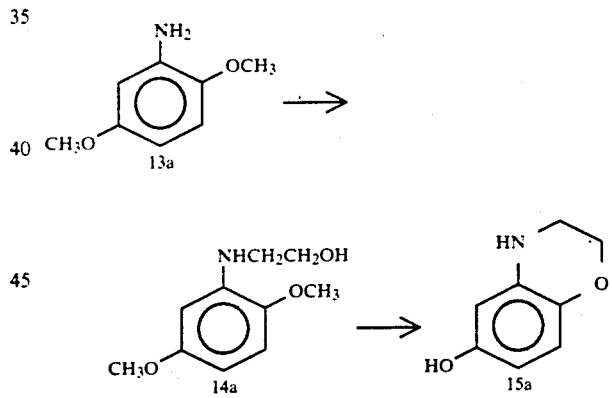

Treatment of 2-methoxy-5-nitroaniline 16a with 2-chloroethyl chloroformate and calcium carbonate in dioxane afforded the carbamate 17a. Rearrangement of 17a followed by an intramolecular cyclization by action of potassium hydroxide in ethanol led to the formation of 6-nitrobenzoxazine 18a. Reduction of 18a with iron in acetic acid produced 6-aminobenzoxazine 19a.

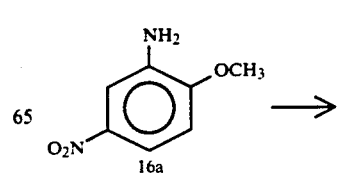

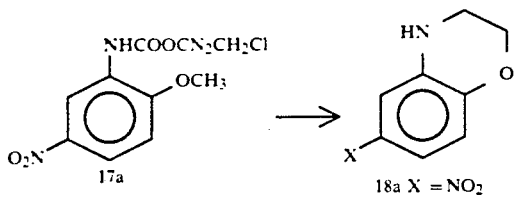

Recently, two procedures have been reported for the synthesis of 1,4-benzoxazine systems by the use of an intramolecular reductive cyclization of nitroketones. Condensation of 20a with benzylamine afforded phenoxy alcohol 21a, which was oxidized with Jones reagent to give the nitroketone 22a. Reductive cyclization of 22a with Raney Ni in ethanol afforded 23a. This was reported in Synthesis 660, 1974 by S. P. Gupta et al.

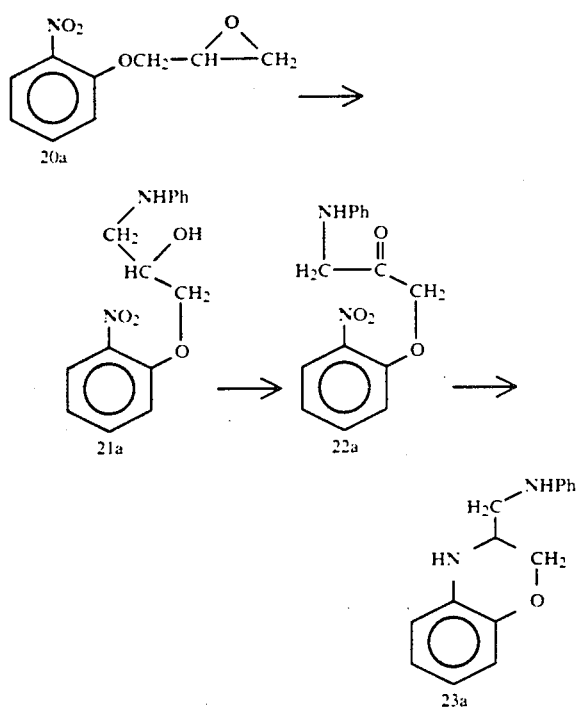

Ph = a phenyl ring

Similarly, compound 24a was converted to 25a by catalytic transfer hydrogenation using NaH$_2$PO$_2$ as hydrogen donor and 5% Pd-C as catalyst in a two phase system (H$_2$O/THF). See P. Battistoni et al, Synthesis 220 (1979).

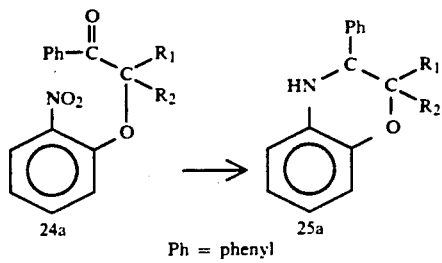

Ph = phenyl

Coudert et. al reported in Synthesis, 541 (1979) a new synthetic approach to 1,4-benzoxazine using solid-liquid phase-transfer catalysis. Cyclocondensation of ortho-hydroxycarboxanilides 26a with 1,2-dibromothane in the presence of powdered NaOH and Aliquat 336 in CH$_3$CN/CH$_2$CCl$_2$ proceeded in high yield to give 27a which, with KOH in MeOH, afforded 28a.

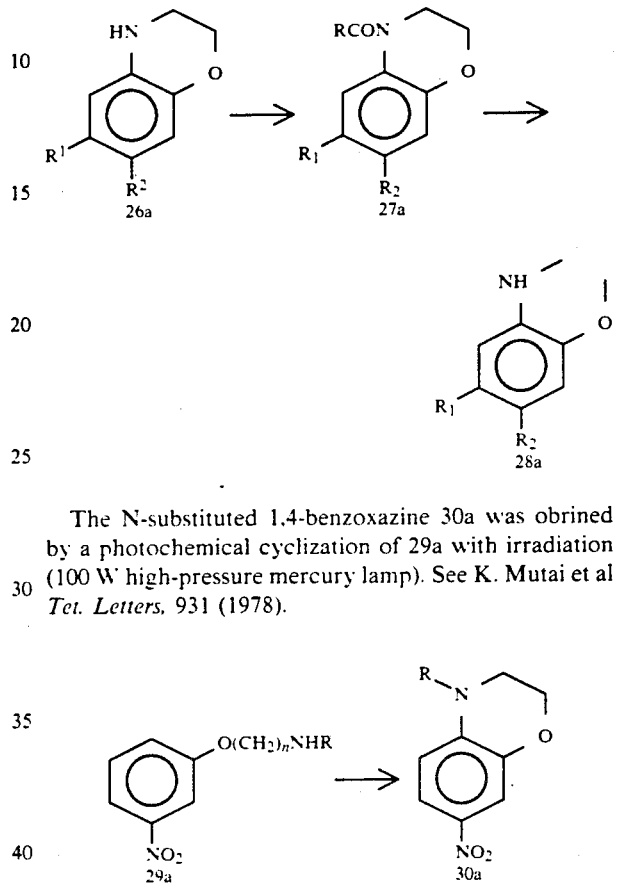

The N-substituted 1,4-benzoxazine 30a was obrined by a photochemical cyclization of 29a with irradiation (100 W high-pressure mercury lamp). See K. Mutai et al Tet. Letters, 931 (1978).

In U.S. Pat. No. 4,552,951, an azo dye was prepared using benzomorpholine couplers and having one or two cinnamoyl substituents. At column 2, lines 37 and 57, NO$_2$ and NH$_2$ are disclosed as substituents on the benzene ring of the bicyclic benzoxazine system.

Chemical Abstracts 106: 138457t (EPO Publication 196, 570) discloses herbicidal compositions containing benzoxazine derivatives.

Chemical Abstracts 106: 102305c recites 7,8-difluoro-3, 4-dihydro-3-methyl-2H-1,4-benzoxazine as a herbicide.

All publications cited herein are hereby incorporated by reference, unless otherwise stated.

While various of these references show compounds which are similar to the structural formulas recited herein, none of them actually teaches the use of applicants' compounds as dyes.

THE INVENTION

It has been discovered that certain benzo-heterocyclic compounds are useful as direct dyes for coloring keratinaceous fibers, eg., human or other hair.

The compounds of the invention conform to formula I:

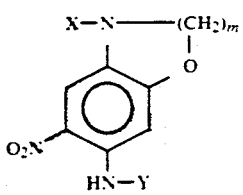

(I)

wherein: X and Y are independently selected from the group consisting of: hydrogen, $C_{1-6}$ alkyl, $C_{1-6}$ alkoxyalkyl, and $C_{1-6}$ aminoalkyl, $C_{1-6}$ hydroxyalkyl, and $C_{1-6}$ hydroxyaminoalkyl; and m=1,2, or 3.

These compounds are novel dyes and are produced via chemical reactions such as those discussed above and set out in the examples.

We have found that the benzoxazine derivatives of the current invention (e.g. those of structure I), while analogs of 2-nitro-p-phenylenediamine and highly substituted, still have absorption maxima in the orange-red region of the spectrum and are, therefore, excellent substitutes for 2-nitro-p-phenylenediamine. In addition, we have found that they show excellent washfastness (i.e., to normal shampooing).

The invention concerns the novel compounds and methods of using same.

ADVANTAGES

The compounds and methods of the invention have several advantages over other systems used in the art.

Specifically, each compound can be used to replace a specific nitroparaphenylenediamine, and the benzoxazines often are superior in washfastness to other nitroparaphenylene diamines, so that the color remains on the treated or dyed substrate through a larger number of washings.

While 2-nitro-p-phenylenediamine undergoes ready nucleophilic substitution of amino groups by monoethanolamine in aqueous system (M. Bil and J. F. Corbett, *Dyes and Pigments* 2,215, 1981), the new dye, e.g. 7, suffers from little amine exchange. This will improve the storage stability of dye formulations.

These and other advantages and aspects of the invention will be better understood after consideration of the following description and claims.

DESCRIPTION OF THE INVENTION

The invention will be described in terms of the compounds and their preparation, as well as in terms of the compositions and methods which use them and the substrates which are colored thereby.

Unless stated otherwise, all percentages stated herein are weight percent (wt. %), based on total composition weight.

COMPOUNDS

The compounds of the invention conform generally to formula I:

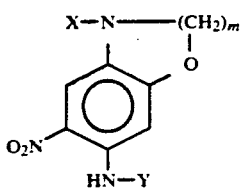

(I)

wherein: X and Y are independently selected from the group consisting of: hydrogen, $C_{1-6}$ alkyl, $C_{1-6}$ alkoxyalkyl, and $C_{1-6}$ amino-alkyl, $C_{1-6}$ hydroxyalkyl, and $C_{1-6}$ hydroxy-aminoalkyl; and m=1, 2, or 3.

Preferred compounds are those conforming to formula II:

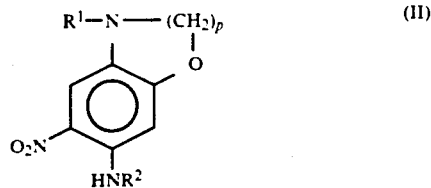

(II)

wherein: p=1, 2, or 3; and $R^1$ and $R^2$ are each independently hydrogen or groups of the formula $C_nH_{2n+1-c}(OH)_c$, wherein n=1-6 and c=0-3.

Useful compounds include, but are not limited to:

A. 7-Amino-6-nitro-3,4-dihydro-2H-1,4-benzoxazine;
B. 7-Amino-4-methyl-6-nitro-3,4-dihydro-2H-1,4-benzoxazine;
C. 7-Amino-4-ethyl-6-nitro-3,4-dihydro-2H-1,4-benzoxazine;
D. 7-Amino-4-(2-hydroxyethyl)-6-nitro-3,4-dihydro-2H-1,4-benzoxazine;
E. 7-Amino-4-(2,3-dihydroxypropyl)-6-nitro-3,4-dihydro-1,4-benzoxazine;
F. 7-(2-Hydroxyethylamino)-6-nitro-3,4-dihydro-2H-1,4-benzoxazine;
G. 7-(2,3-Dihydroxypropylamino)-6-nitro-3,4-dihydro-2H-1,4-benzoxazine; and
H. 4-(2-Hydroxyethyl)-7-(2-hydroxyethylamino)-6-nitro-3,4-dihydro-2H-1,4-benzoxazine.

Highly preferred compounds are those conforming to formula II, in which p=2. Compounds of formula II in which $R_1$ and $R_2$ are either hydrogen, $C_{1-6}$ alkyl, or, with $C_nH_{2n+2-c}(OH)_c$, with n and c being as defined above, are among the highly preferred compounds. The most preferred compounds are A, D, F, and H, above.

Mixtures of compounds of formula I with each other and other colorants are contemplated.

PREPARATION OF COMPOUNDS

The preparation of compounds of the invention involves a series of chemical reactions which are each individually known. Compounds of formula I can be prepared by four routes shown in Schemes I, II, III and IV in Example 1.

DETAILED DESCRIPTION OF THE INVENTION

The direct dyes of the present invention are suitable for incorporation in hair dye- or surface active agent-containing compositions comprising one or more of the following: solvents, surfactants or surface-active agents, thickeners, antioxidants, preservatives, fragrances, and other constituents typically employed in hair dye compositions.

In addition, as was mentioned above, dye compositions may also contain one or more additional dye component(s), the admixture of dyes (including the dye of the present invention) providing the desired shade.

The compositions of the present invention may also contain one or more hair conditioning agents. Such conditioning agents are typically cationic in character and include cationic surface-active agents and cationic polymeric materials. The dyes of the present invention might also be incorporated into an oxidation dye base, to obtain a desired shade.

The constituents includable in the hair dye compositions of the present invention are generally within the ranges set out below.

TABLE

| Constituents | Broad Range Wt. % | Preferred Range Wt. % |
| --- | --- | --- |
| Dyes of the invention | 0.001-5 | 0.01-1 |
| Other dyes | 0-10 | 0.01-4 |
| Surfactants | 0-25 | 0.1-5 |
| Thickening agents | 0-20 | 0.1-5 |
| Nonaqueous solvent(s) | 0-40 | 1-10 |
| pH Modifiers | 0-20 | 0.05-5 |
| Fragrance | 0-5 | 0.05-1 |
| Water | q.s. 100 | q.s. 100 |

In practice, the dyes employed in this invention will generally be used with other dyes. The amount of the dyes used would depend on the lightness or darkness of the desired shade, as well as on the desired tonality.

In carrying out the present invention, any of the nitrobenzoxazine dyes described above, or combinations thereof, are incorporated in a fluid hair dye vehicle of the type suitable for applying direct-dyeing dyes. A large number of such vehicles are known to those in this art. These may vary from simple aqueous solutions and/or suspensions of the dye to very sophisticated aqueous compositions such as creams, mousses, lotions, pastes, gels, and the like. Often, the compositions of the present invention contain, in addition to the subject dyes herein disclosed, a second dye or a blend of other dyes, nonionic and anionic surfactants, solvents, thickeners, antioxidants, preservatives, fragrances, etc. In these aqueous compositions, the carriers or vehicles may be water or a combination of water with other solvents, e.g., ethanol. The dyes may also be employed in aerosol systems, e.g., an aerosol emulsion system in which the dye is contained in an aqueous phase of the system. See, for example, U.S. Pat. No. 4,021,486 to Halasz, et al.

The nitrobenzoxazine dyes employed in the present invention can be employed to prepare basic, neutral or acidic dye compositions. Furthermore, they may be included in hair dyeing compositions which contain other direct dyeing dyes. A variety of the direct dyeing colorants known in the prior art are useful for this purpose. They include nitro dyes, azo dyes, anthraquinone dyes, etc.

By way of illustration, any of the nitro dyes disclosed in the following U.S. Patents may be used in conjunction with the present dyes: U.S. Pat. Nos.: 2,750,326; 2,750,327; 3,088,877; 3,088,878; 3,088,978; 3,642,423; 3,950,127; 4,125,601; 4,432,769, and 4,337,061.

The pH of the present dye compositions can vary from about 4 to about 12 and preferably from about 7 to about 11.5, and may be obtained by adjustment with a suitable pH modifying agent. The compositions herein may also contain buffering agents which maintain the pH within a particular range.

When the compositions are preferably to be basic, an alkalizing agent can be employed over a wide range, depending on the dye and particular alkalizing agent employed and the desired pH. Illustratively, the alkalizing agent can vary between about 0 and about 20%, preferably from about 0.05 to about 5%, and most preferably from about 0.10 to about 2%, by weight of the composition. Any of a wide variety of alkalizing agents can be used to adjust the pH of the present dyeing composition on the basic side.

Ammonium hydroxide or aqueous ammonia, because of its freedom from toxicity over a wide concentration range and its economy, is an acceptable alkalizing agent. However, there can be used as an alkalizing agent, in place of, or together with, ammonia, any other compatible amine or ammonia derivative such as an alkylamine, e.g., ethylamine, dipropylamine, or triethylamine; an alkanediamine, e.g., 1,3-diaminopropane; an alkanolamine, e.g., monoethanolamine or diethanolamine, triethanolamine, a polyalkylene polyamine, e.g., diethylenetriamine; or a heterocyclic amine, such as morpholine. Mixtures can be used.

The pH of the composition may be adjusted on the acid side with any inorganic or organic acid or acid salt which is compatible with the composition and will not introduce toxicity under its conditions of use, especially when acid compositions are desired. Illustrative of acids or acid salts there can be mentioned are: sulfuric, formic, acetic, oleic, lactic, citric or tartaric acid, or ammonium sulfate, sodium dihydrogen phosphate or potassium bisulfate. Illustratively, the amount of acidifying agent present is from about 0 to about 5%, and preferably from about 0.05 to about 1%.

The alkalizing, acidifying and buffering agents discussed herein are referred to as "pH modifiers".

Surface active agents can also be employed in the dyeing compositions of this invention. These can be anionic, nonionic or cationic. By way of example of the various types of surface active agents, there can be mentioned: higher alkylbenzene sulfonates; alkylnaphthalenesulfonates; sulfonated esters of alcohols and polybasic acids; taurates; fatty alcohol sulfates; sulfates of branched chain or secondary alcohols; alkyldimethylbenzylammonium chlorides, salts of fatty acids or fatty acid mixtures; N-oxyalkylated fatty acid alkanolamides, and the like.

Illustrative of specific surfactants that can be mentioned are: sodium lauryl sulfate; polyoxyethylene lauryl ester; myristyl sulfate; glyceryl monstearate; triethanolamine oleate, the sodium salt of palmitic methyl taurine; cetyl pyridinium chloride; lauryl sulfonate; myristyl sulfonate; lauric diethanolamide; polyoxyethylene stearate; ethoxylated oleyl diethanolamide; polyethylene glycol amides of hydrogenated tallow; stearyldimethylbenzyl ammonium chloride; dodecylbenzene sodium sulfonate; 2-amino-2-methyl propanol; the triethanolamine salt of p-dodecylbenzene sulfonate; the triethanolamine salt of p-dodecylbenzene sulfonate; nonylnaphthalene sodium sulfonate; dioctyl sodium sulfosuccinate; sodium N-methyl-N-oleoyl taurate; the oleic acid ester of sodium isethionate; sodium dodecyl sulfate; the sodium salt of 3-0-diethyl tridecanol-6-sulfate and the like.

The quantity of surface active agent can vary over a wide range, such as that of from about 0.05% to about 15%, and preferably from about 0.10 to about 5%, by weight of the composition.

A thickening agent may also be incorporated in the dyeing compositions of this invention. It may be one or several of those commonly used in hair dyeing. These are exemplified by such things as sodium alginate or gum arabic, or cellulose derivatives, such as methylcellulose, e.g., Methocel 60 HG, or the sodium salt of carboxymethylcellulose, or hydroxyethyl-cellulose, e.g., Cellosize QP-40 or acrylic polymers, such as polyacrylic acid sodium salt, or inorganic thickeners, such as bentonite. Mixtures are operable.

The quantity of thickening agent can also vary over a wide range, such as that of from about 0.1 to about 20%. Ordinarily, the thickening agent concentration will range from about 0.5 to 5% by weight of the total composition. The viscosity of the composition may vary from about 1 cp to about 100,000 cps. For a typical lotion formulation, composition viscosity is between about 100 cps to about 10,000 cps.

It is also useful to incorporate an antioxidant in the present dye compositions. A variety of antioxidants are known in the prior art which would be useful for this purpose. Among these, mention may be made of the inorganic sulfites, e.g., sodium sulfite, thioglycollic acid and other mercaptans, butylated hydroxytoluene, sodium dithionite, various forms of ascorbic acid and its derivatives, e.g., sodium ascorbate, erythorbic acid, ascorbyl palmitate, ascorbyl laurate, etc.

The quantity of antioxidant, when used, can vary quite a bit. However, this will, in general, be on the order of about 0.001 to 1% by weight.

The nitrobenzoxazine dyes are incorporated in compositions of this invention in tinctorially effective quantities, i.e., in concentrations which are adequate to color the hair. These quantities can vary over a wide range, but ordinarily they will constitute from about 0.001 to greater than about 5%, e.g., 10%, by weight of the composition. However, the quantity will preferably be from about 0.05 to about 2%, most preferably about 0.1 to about 2 wt. %, of the composition.

The major constituent of the composition employed is usually water, and this can vary in amount over a wide range dependent in large measure on the quantity of other additives. Thus, the water content can be as little as 10%, but preferably will amount to from about 70 to 99% by weight of the composition.

The dyeing compositions of this invention are preferably aqueous compositions. The term "aqueous composition" is used herein in its usual generic sense as embracing any water-containing composition useful for the present purposes. This includes true solutions of the dye in an aqueous medium, either alone or in conjunction with other materials, which are also dissolved or dispersed in the aqueous medium. The term "aqueous composition" also emcompasses any mixture of dye with the aqueous medium, either alone or together with other ingredients. The dye may be colloidally dispersed in the medium or may merely be intimately mixed therein.

Moreover, the aqueous medium may comprise water or water and an additional or auxiliary solvent. The latter may be employed as a common solvent to enhance the solubility of the dye or some other organic material. Other auxiliary solvents which may be used for this purpose include ethanol, carbitol, isopropanol, propylene glycol, ethylene glycol, diethylene glycol, diethylene glycol monoethyl ether, glycerine, and the like and mixtures thereof.

The nitrobenzoxazine dye(s) and any of the surface active agents, thickening agents, and combinations thereof set forth above may be used in the proportions specified in the Table I.

The aqueous dyeing compositions of this invention can be prepared by the conventional methods used in the hair dyeing art. Thus, they can be prepared by dissolving or suspending the dye in water in the desired concentrations. Water miscible organic solvents, such as aliphatic $C_{1-4}$ alcohols, e.g., ethanol or glycol ethers, can be employed to facilitate solution of the dye. In one process, the dye can be dissolved first in the solvent and this solution then diluted with water.

The dispersion of the various ingredients can also be facilitated by heating the composition at temperatures varying from about 40° C. to about 110° C., either before dilution with water or afterwards. The concentrations of co-solvents or diluents will be from about 5% to about 95%, depending upon storage, handling, and application considerations.

The colorants of the invention may be used in combination with oxidation dyes. The compounds of formula I are used for the purpose of highlighting the final dyeing. These compositions contain at least one direct dye of formula I and oxidation dye precursors consisting of developers and couplers well-known in the hair-coloring art (e.g. p-phenylenediamines, m-phenylenediamines, resorcinol). The concentration of dye precursors ranges from about 0.001 to about 5% by weight.

In use, the dye mixture is mixed with hydrogen peroxide solution (about 0.1 to about 10% w/w/) immediately prior to application to the hair.

The colorants of the invention can also be used in combination with other direct dyes, such as azo, anthraquinone and nitro dyes, in a process of direct dyeing of hair. The concentration of these other dyes ranges from about 0.001 to about 5% by weight.

Other conventional additives, ie, excipients (e.g., perfumes, thickeners, surfactants, stabilizers), and the like can be beneficially employed in the compositions of the invention. When present, they will be used in quantities ranging from about 0.5 to about 55 wt. %.

METHODS OF COLORING

The compounds of the invention are useful in various conventional methods of coloring keratinaceous substrates. Accordingly, the substrates may be contacted with the color-containing formulation via dipping, spraying, painting, dabbing, application of gels, mousses, powders, etc.

When applied to living hair on the human head, the compositions can be applied to the hair with a brush, sponge, or other means of contact, such as pouring the composition directly onto the hair until saturated. The reaction time, or time of contact of the dyeing composition with the hair, is not critical and can vary over a wide range used in the hair dyeing art, such as periods of about 5 minutes to about 2 hours. Preferably, a period of from about 5 minutes to about 60 minutes is utilized, and most often a period of about 20 to about 40 minutes.

The dyeing temperature can vary over wide limits as is conventional in the art. Thus, the dyeing temperature can vary from about room temperature, e.g., about 20° to about 60° C., and preferably from about 20° to about 45° C. At the end of the time period, the composition is rinsed from the hair with water, although a weak acid solution may be employed as the rinse.

One preferred sequence of steps by which colorant formulations in accordance with the invention are contacted with human hair involves:
(1) Mix or otherwise prepare dyeing solution with oxidant, if appropriate.
(2) Apply developer to the hair.
(3) Rinse.
(4) Shampoo.
(5) Optionally, repeat steps (2)-(4).

SUBSTRATES

Substrates to be colored in accordance with the invention are generally fibrous ones of keratinaceous character. Accordingly, the hair and fur of mammals are typical. Preferred is human hair, which hair may be upon a human head (i.e., "living" hair) or in a wig, or hair piece. "Living" human hair is one highly preferred substrate or surface to be colored.

It should be appreciated that such factors as the porosity, color, etc. of the hair may alter the formulation and/or method of coloring used. Chemically relaxed hair, for example, is highly porous and may not need as high a concentration of colorant and/or as long a contacting time as non-relaxed hair. Similarly, blonde or grey hair may require less rigorous treatment than brown or grey-brown hair because of the lower content of melanin therein.

The following examples will serve to illustrate the invention.

EXAMPLE 1

This example describes methods of making various compound set out supra: The overall reaction scheme is:

A. Scheme I

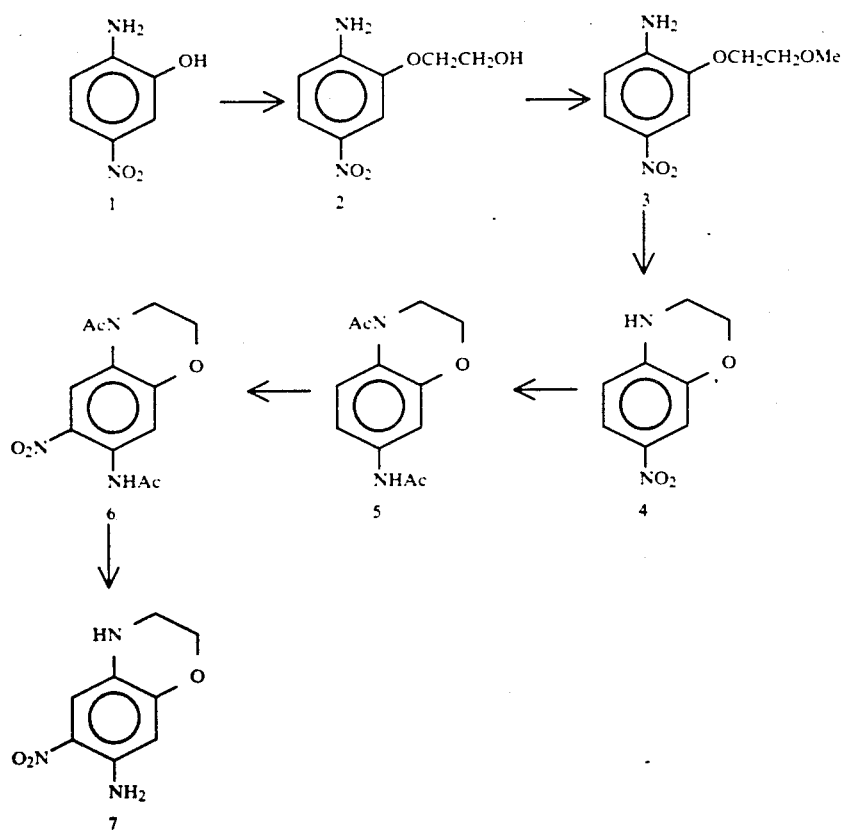

Compound 7, 7-amino-6-nitro-2H-1,4-benzoxazine, can be prepared in six steps from commercially available 2-amino-5-nitrophenol. O-Alkylation of 1 with 2-haloethanol (BrCH$_2$OH or ClCH$_2$CH$_2$OH) with base (K$_2$CO$_3$, Na$_2$CO$_3$, KOH, NaOH, etc.) will afford 2.

Mesylation of 2 will give the mesylate 3 which can be converted to 7-nitro-2H-1,4-benzoxazine 4. Compound 6 can be prepared by a sequence of reactions: 1) hydrogenation, 2) acetylation, and 3) nitration. Hydrolysis of 6 with acid will give 7.

B. Scheme II

The key intermediate 4 will be also prepared by the following route.

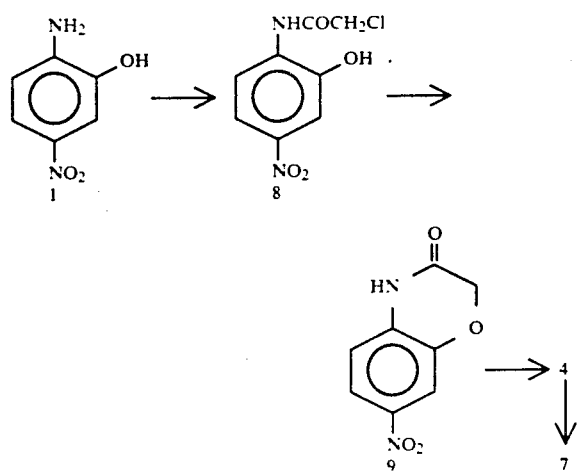

The synthesis of 9 is known in the literature (G. Newberg and M. A. Phillips, *J. Chem. Soc.*, 3046, 1928). Reduction of 9 with borane-tetrahydroguran complex described in the literature (M. E. Jung and J. C. Rohloff, *J. Am. Chem. Soc.*, 50, 4909, 1985) will afford 4. The compound 4 will be further transformed into 7 by the route described in Scheme I.

C. Scheme III

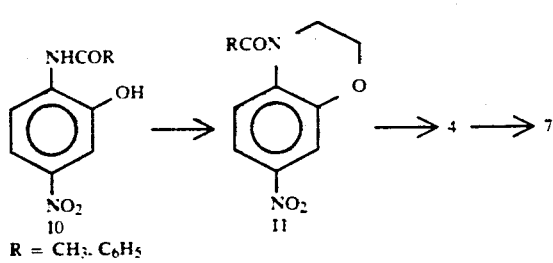

R = CH₃, C₆H₅

Compound 4 can be prepared by the procedure described in the literature (G. Coudert, G. Guillaumet, and B. Loubinous, *Synthesis*, 541, 1979). Compound II can be prepared from 10 by treatment with dibromoethane and base in the presence of a phase-transfer catalyst. Hydrolysis of 11 will give 4.

D. Scheme IV

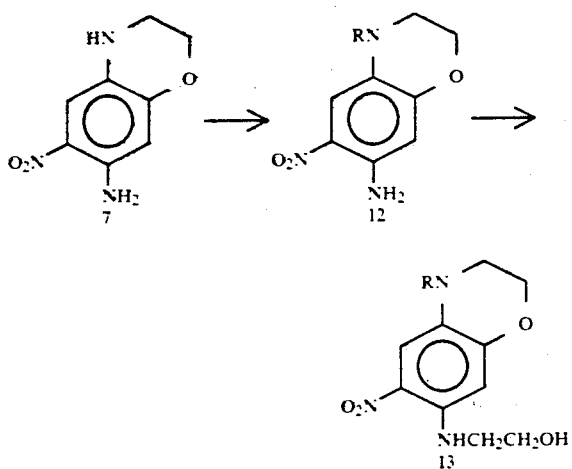

4-Substituted compounds such as B, C, D and E can be prepared by means of N-alkylation using alkyl halide (CH₃I, CH₃CH₂I, BrCH₂CH2OH, BrCH₂CH₂(OH)C-H₂OH and base (K₂CO₃, NaOH or KOH, etc.). Selective alkylation of C-7 amino group with alkyl halide (4-position may require protection) will provide F and G. Compound H can be prepared conveniently by treatment of A with ethylene oxide.

EXAMPLE 1

Scheme I

2-(2-Hydroxyethoxy)-4-nitroaniline 2

A mixture of 2-amino-5-nitrophenol (1, 30 g), 2-chloroethanol (24.2 g) and sodium hydroxide (powdered, 12 g) in DMSO (100 ml) was stirred for 2.5 h at 110° C. The mixture was poured onto crushed ice (200 g) and the dark yellow precipitate was filtered, washed with H₂O three times. Recrystallization from ethanol gave 22.4 g (58%) of 2: mp 140°-142° C.; MS m/e 198 (M+).

2-(2-Mesyloxyethoxy)-4-nitroaniline 3

To a stirred suspension of 2 (42 g) and triethylamine (30.4 g) in dichloromethane (400 ml) in an ice bath was added dropwise a solution of methanesulfonyl chloride (25.2 g) in dichloromethane (100 ml). The mixture was stirred for 30 min. and the precipitate was collected by filtration and recrystallized from ethyl acetate to give 33.77 g (58%) of 3: mp 132°-135° C.; MS m/e 276 (M⁻).

7-Nitro-3,4-dihydro-4H-1,4-benzoxazine 4

A mixture of 3 (25 g) and potassium hydroxide (7.6 g) in DMSO (200 ml) was stirred at 80° C. for 2 h and poured onto crushed ice (300 g). The resulting yellow precipitate was collected by filtration, washed with water three times and dried under reduced pressure to give 12.8 g (79%) of 4: mp 175°-177° C.; MS m/e 180 (M+).

4-Acetyl-7-acetamido-3,4-dihydro-2H-1, 4-benzoxazine 5

A mixture of 4 (8.0 g) and 10% Pd-C (0.8 g) in ethyl acetate (150 ml) was hydrogenated at 60 psi for 1 h. The mixture was filtered over Celite into ethyl acetate (50 ml) containing triethylamine (25 ml) and acetic anhydride (25 ml) and washed with ethyl acetate. After completion of acetylation (usually 1.5 h), the mixture was washed with brine and water, dried (Na₂SO₄) and evaporated to give 8.2 g (79%) of 5 as a white solid: mp 150°-154° C.; MS m/e 234 (M⁺).

4-Acetyl-7-acetamido-6-nitro-3,4-dihydro-2H-1,4-benzoxazine 6

To a stirred solution of 5 (5.0 g) in acetic anhydrid (50 ml) in an ice bath was added slowly fuming nitric acid (5 ml). The mixture was stirred for 0.5 h and the yellow precipitate was filtered, washed with water three times and dried under reduced pressure to give 4.9 g (82%) of 6: mp 199°-202° C.; MS m/e 279 (M⁺).

7-Amino-6-nitro-3,4-dihydro-2H-1, 4-benzoxaxine 7

A mixture of 6 (9.8 g) and C-HCl (50 ml) was stirred at 90° C. for 1.5 h and poured onto crushed ice. The mixture was neutralized with aqueous potassium hydroxide to reach pH 4.6. The dark red solid was collected by filtration, washed three times with H₂O and dried under reduced pressure to give 5.31 g (78%) of 7: mp 111°-114° C.; MS m/e 195 (M+); ¹H NMR(DM50-d6) 3.18 (m, 2H), 4.19 (m, 2H), 5.71 (bs, 1H), 6.27 (s, 1H), 6.99 (bs, 2H) 7.14 (s, 1H). UV max 475 m (95%E-tOH) (log 3.61).

EXAMPLE 2

Scheme II

2-Chloroacetamido-5-nitrophenol 8

To a stirred solution of 1 (18 g) in acetone (135 ml) at room temperature was added dropwise a solution of chloroacetyl chloride (10.8 ml) in acetone (10 ml) over a period of 15 min. The mixture was stirred for another 30 min. and poured onto crushed ice (300 g). The white precipitate was collected and washed with H₂O to give 9 (24.3 g, 90%): mp 233° C.; MS m/e 230 (M+).

7-Nitro-3-oxo-3,4-dihydro-2H-1,4-benzoxazine 9

A mixture of 8 (22 g) and powdered KOH (6.9 g) in DMSO (100 ml) was stirred at 95° C. for 30 min. and poured onto crushed ice (400 g). The resulting precipitate was collected and washed with H₂O to give 9 (15.7 g, 85%): mp 230°-232° C.; MS m/e 194 (M+).

7-Nitro-3,4-dihydro-2H-1,4-benzoxazine 4

To 9 (10 g) at room temperature was added portionwise 1M solution of borane-tetrahydrofuran complex (52 ml) over a period of 15 min. The mixture was heated to reflux for 10 min. and poured onto crushed ice (200 g). The resulting orange precipitate was collected and washed with water to give 4 (8.9 g, 95.9%).

EXAMPLE 3

Compound 7, produced in Example 1, was used to color hair as follows:

A composition was prepared containing:

| | |
|---|---|
| 0.05 g | Compound 7 |
| 10.00 g | Water |
| 10.00 g | Ethanol (95%) |

The composition was used to dye swatches of blended gray hair. The hair was soaked in the dye solution for 30 minutes and then rinsed with water.

The hair was then subjected to a series of five shampoos and water rinses to determine washfastness. The Hunter Tristimulus values of the dyed and shampooed hair are recorded in the table below.

| | Tristimulus Values | | |
|---|---|---|---|
| | L | a | b |
| Undyed | 33.06 | −0.47 | 7.31 |
| Initial | 28.31 | 7.96 | 7.39 |
| Shampooed | 28.38 | 7.63 | 7.40 |

In the Hunter Tristimulus System, "L" is a measure of lightness and darkness, that is, the depth of the color of the hair tress. The lower the value of L, the darker the color.

A decrease in the value of L indicates a darkening of the hair tress. In the case of bleached and blended gray hair, a lowering of L shows deposition of hair dye on the tress.

The table shows that the blended gray hair tresses were colored to a substantial degree by the dye. Moreover, it is seen that the shampooings did not significantly increase the values of L in the several tests, indicating good washfastness for the dye.

The "a" value is a measure of the greenness or redness of the hair's color. As the a value increases, the hair has a more prominent red tonality. A lowering in the a value results in greener shades.

The value of "b" is a measure of the blueness or yellowness of the hair color. As the b value increases, the hair tress is more yellow.

Neither the a nor the b values changed significantly due to shampooing.

Based on these results, it is seen that Compound 7 would be very desirable in a semipermanent hair dye composition.

EXAMPLE 4

| Hair Dye Composition (Composition A) | |
|---|---|
| 0.32 g | Compound 7 |
| 5.00 g | 95% ethanol |
| 0.50 g | Hydroxyethyl Cellulose |
| 1.50 g | Triethanolamine |
| 88.00 g | Water |
| 95.32 g | |

The composition has a pH of 9.7. When applied for 30 min. to bleached hair and blended gray hair, this mixture imparts to the hair an orange-red coloration after rinsing and shampooing. Each shampooing step involved both washing and rinsing.

For comparison purposes, the following composition (composition B) containing 2-nitro-p-phenylenediamine was formulated.

| | |
|---|---|
| 0.25 g | 2-nitro-p-phenylenediamine |
| 5.00 g | 95% ethanol |
| 0.50 g | Hydroxyethyl Cellulose |
| 1.50 g | Triethanolamine |
| 88.00 g | Water |
| 95.25 g | |

The composition has a pH of 9.7. Bleached and blended gray hair were dyed as described in Example 1 to give red coloration.

| | | Hunter Tristimulus Values | | |
|---|---|---|---|---|
| | | L | a | b |
| Compound 7 | G | 23.65 | 16.58 | 8.00 |
| (Compn A) | B | 22.33 | 22.98 | 8.88 |
| 2-NO$_2$-ppd | G | 18.08 | 15.09 | 6.02 |
| (Compn B) | B | 20.97 | 21.11 | 8.26 |

G Blended gray hair
B Bleached hair

EXAMPLE 5

Hair dyeing compositions were made up using the following:

| | Compn. C | Compn. D |
|---|---|---|
| Nonoxynol 4 | 10.50 g | 10.50 |
| Nonoxynol 9 | 12.00 | 12.00 |
| Oleic Acid | 2.00 | 2.00 |
| Propylene Glycol | 1.50 | 1.50 |
| 95% Ethanol | 5.00 | 5.00 |
| EPTA | 1.25 | 1.25 |
| Sodium Bisulfite | 0.18 | 0.18 |
| Ammonium Hydroxide | 3.25 | 3.25 |
| Water | 13.06 | 13.17 |
| p-Phenylenediamine | 0.02 | 0.02 |
| p-Aminophenol | 0.30 | 0.30 |
| 5-Amino-o-cresol | 0.43 | 0.43 |
| Compound 7 | 0.51 | 0.00 |
| 2-Nitro-p-phenylenediamine | 0.00 | 0.40 |
| Total: | 50.00 g | 50.00 g |

Both compositions have a pH of 9.7.

Hair dye composition C described above was mixed with 50 g of 20 volume hydrogen peroxide. The mixture was allowed to react on bleached and blended gray hair for 30 min. at room temperature. The hair was colored red.

The Composition D containing 2-nitro-p-phenylenediamine rendered hair a red shade, similar to that obtained from C.

EXAMPLE 6

Dye Stability Test

This example shows the stability, ie., non-reactivity of the subject compounds where reaction with monoethanolamine is concerned. A mixture of 7 (0.97 g) and monoethanolamine (1.04 g) in water (10 ml) was stirred at 110° C. for 7 days. The conversion to 14 was not observed.

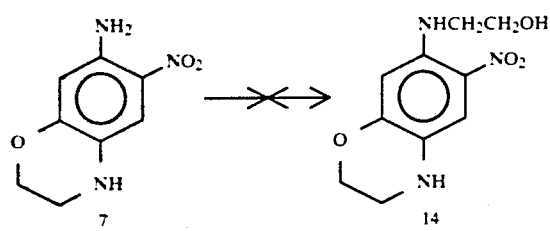

Under the same conditions, 2-nitro-p-phenylenediamine 15 underwent nucleophilic substitution with monoethanolamine to give 16. 16 was further converted to 6-aminoquinoxaline 17. See M. Bil and J. Corbett, *Dyes and Pigments* 2, 215, 1981.

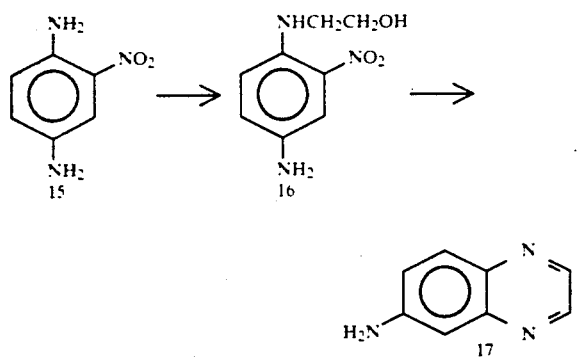

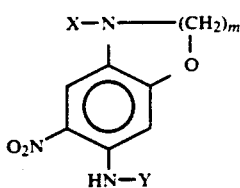

Reasonable variations, such as those which would occur to a skilled artisan, can be made herein without departing from the scope of the invention.

We claim:

1. Compounds of Formula I

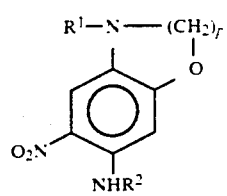

wherein: X and Y are independently selected from the group consisting of: hydrogen, $C_{1-6}$ alkyl, $C_{1-6}$ alkoxy alkyl, $C_{1-6}$ aminoalkyl, $C_{1-6}$ hydroxyalkyl, and $C_{1-6}$ hydroxyaminoalkyl; and m=1.

2. Compounds of claim 1 conforming to Formula II

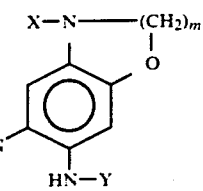

wherein: p=1; and $R^1$ and $R^2$ are each independently hydrogen or groups of the formula $C_nH_{2n+1-c}(OH)_c$, wherein n=1-6 and c=0-3.

3. A composition for dyeing keratinaceous substrates containing in the dye component at least one compound of Formula I

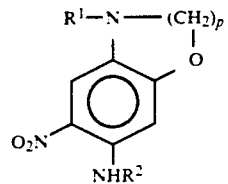

wherein X and Y are independently selected from the group consisting of: hydrogen, $C_{1-6}$ alkyl, $C_{1-6}$ alkoxy alkyl, $C_{1-6}$ aminoalkyl, $C_{1-6}$ hydroxyalkyl, and $C_{1-6}$ hydroxyaminoalkyl; and m=1.

4. The composition of claim 3 wherein the dye component contains at least one compound of Formula II

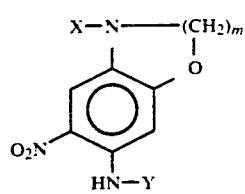

wherein p=1; and $R^1$ and $R^2$ are each independently hydrogen or groups of the formula $C_nH_{2n+1-c}(OH)_c$, wherein n=1-6 and c=0-3.

5. A method of dyeing a keratinaceous substrate comprising the step of contacting the substrate with at least one dye of Formula I

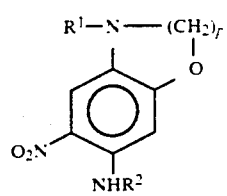

wherein: X and Y are independently selected from the group consisting of: hydrogen, $C_{1-6}$ alkyl, $C_{1-6}$ alkoxy alkyl, $C_{1-6}$ aminoalkyl, $C_{1-6}$ hydroxyalkyl, and $C_{1-6}$ hydroxyaminoalkyl; and m=1.

6. The method of claim 5 wherein the substrate is human hair.

7. The method of claim 6 wherein the dye is of Formula II

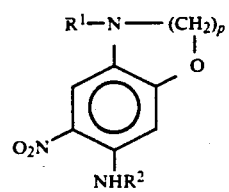

wherein: p=1; and $R^1$ and $R^2$ are each independently hydrogen or groups of the formula $C_nH_{2n+1-c}(OH)_c$, wherein n=1-6 and c=0-3.

* * * * *